United States Patent
Ågerup

(10) Patent No.: US 8,721,622 B2
(45) Date of Patent: May 13, 2014

(54) USE OF A VISCOELASTIC COMPOSITION FOR TREATING INCREASED INTRAOCULAR PRESSURE

(75) Inventor: Bengt Ågerup, Paris (FR)

(73) Assignee: Q-MED AB, Uppsala (SE)

( * ) Notice: Subject to any disclaimer, the term of this patent is extended or adjusted under 35 U.S.C. 154(b) by 487 days.

(21) Appl. No.: 11/579,621

(22) PCT Filed: May 4, 2005

(86) PCT No.: PCT/SE2005/000663
§ 371 (c)(1),
(2), (4) Date: Apr. 19, 2007

(87) PCT Pub. No.: WO2005/105037
PCT Pub. Date: Nov. 10, 2005

(65) Prior Publication Data
US 2008/0058760 A1  Mar. 6, 2008

(30) Foreign Application Priority Data
May 5, 2004 (SE) ........................ 0401182

(51) Int. Cl.
*A61M 31/00* (2006.01)

(52) U.S. Cl.
USPC ............................ 604/521; 604/264; 604/294

(58) Field of Classification Search
USPC ........................ 604/289, 290, 294, 521, 8, 264
See application file for complete search history.

(56) References Cited

U.S. PATENT DOCUMENTS

| | | | |
|---|---|---|---|
| 2,774,239 A | 12/1956 | Fitzgerald | |
| 4,716,154 A | 12/1987 | Mälson et al. | |
| 4,955,883 A | 9/1990 | Nevyas et al. | |
| 4,965,253 A * | 10/1990 | Goldberg et al. | 424/78.36 |
| 5,092,837 A | 3/1992 | Ritch et al. | |
| 5,273,056 A * | 12/1993 | McLaughlin et al. | 128/898 |
| 5,328,481 A * | 7/1994 | Wang | 604/506 |
| 5,360,399 A | 11/1994 | Stegmann et al. | |
| 5,360,425 A * | 11/1994 | Cho | 606/8 |

(Continued)

FOREIGN PATENT DOCUMENTS

| EP | 1 129 683 A1 | 9/2001 |
|---|---|---|
| FR | 2819722 A | 7/2002 |

(Continued)

OTHER PUBLICATIONS

Strubbe, Todd. "Uveitis and pupillary block glaucoma in an aphakic dog." Veterinary Ophthalmology (2002) 5, 1, 3-7.*

(Continued)

*Primary Examiner* — Bhisma Mehta
*Assistant Examiner* — Brandy S Lee
(74) *Attorney, Agent, or Firm* — Buchanan Ingersoll & Rooney P.C.

(57) ABSTRACT

A viscoelastic medium is useful for the manufacture of a medicament, such as a medical device, for treatment of increased intraocular pressure in the eye of a human or animal. The medicament is administerable into at least one sclerally penetrating fistula of the eye such that the fistula is filled with the medicament. The medium is also useful in a method of treating increased intraocular pressure in the eye of a human or an animal in need thereof, comprising the step of injecting the viscoelastic medium into at least one sclerally penetrating fistula in the eye such that the fistula is filled with the medium.

23 Claims, 3 Drawing Sheets

(56) References Cited

U.S. PATENT DOCUMENTS

| | | | |
|---|---|---|---|
| 5,707,643 A * | 1/1998 | Ogura et al. | 424/428 |
| 5,811,453 A | 9/1998 | Yanni et al. | |
| 5,827,937 A | 10/1998 | Ågerup | |
| 6,142,969 A | 11/2000 | Nigam | |
| 6,375,642 B1 | 4/2002 | Grieshaber et al. | |
| 6,383,219 B1 | 5/2002 | Telandro et al. | |
| 6,397,849 B1 * | 6/2002 | Bowman et al. | 128/898 |
| 6,495,608 B1 | 12/2002 | Asgharian | |
| 6,558,342 B1 | 5/2003 | Yaron et al. | |
| 2002/0072673 A1 * | 6/2002 | Yamamoto et al. | 600/452 |
| 2002/0111603 A1 | 8/2002 | Cheikh | |
| 2003/0211166 A1 | 11/2003 | Yamamoto et al. | |
| 2007/0292473 A1 | 12/2007 | Cheikh | |

FOREIGN PATENT DOCUMENTS

| | | |
|---|---|---|
| RU | 2207845 C2 | 7/2003 |
| WO | WO 92/00745 A | 1/1992 |
| WO | WO 97/04012 A1 | 2/1997 |
| WO | WO 98/26777 | 6/1998 |
| WO | WO 2004/026347 A3 | 4/2004 |

OTHER PUBLICATIONS

Johnson, D.H. et al., *Archives of Ophthalmolog*, vol. 120, No. 1, Jan. 2002, pp. 67-70, "Glaucoma Surgery and Aqueous Outflow: How does Nonpenetrating Glaucoma Surgery Work". Discussed at p. 2 of Applicants' Specification.

Raitta, Christina et al, *Acta Ophthalmologica*, vol. 66, (1988), pp. 544-551, "Effects of Intracamerally or Subconjunctivally Injected Cross-Linked Hyaluronic Acid on the Intraocular Pressure and on the Anterior Segment of the Rabbit Eye". Discussed at p. 4 of Applicants' Specification and cited in the Jan. 30, 2006 International Search Report.

Fukasaku, Hideharu M.D. et al., *International Ophthalmology Clinics*, 2001, 41(2), pp. 133-141, "Anterior Ciliary Sclerotomy with Silicone Expansion Plug Implantation: Effect on Presbyopia and Intraocular Pressure".

Netland, Peter A. et al., *American Academy of Ophthalmology*, 2001, 108(2), pp. 416-421, "Nonpenetrating Glaucoma Surgery".

Canadian Search Report, dated Apr. 5, 2012.

* cited by examiner

USE OF A VISCOELASTIC COMPOSITION FOR TREATING INCREASED INTRAOCULAR PRESSURE

TECHNICAL FIELD OF THE INVENTION

The present invention relates to the field of medicine. More specifically, the invention is concerned with the field of ophthalmology. The invention provides a novel method of treating increased intraocular pressure (IOP) in the eye of a human or an animal and a medicament, such as a medical device, that is useful in the method.

BACKGROUND OF THE INVENTION

Glaucoma is caused by a number of different eye diseases that, in most cases, produce increased pressure within the eye. This elevated pressure is caused by a backup of fluid in the eye, and will, over time, cause damage to the optic nerve.

Glaucoma may be treated by medicaments daily in order to down-regulate aqueous humour production or increase outflow of aqueous humour. Alternatively, the glaucoma may be treated by surgery in order to allow for drainage of the aqueous humour and thereby lower the IOP.

Laser surgery (laser trabeculoplasty) is currently the major surgical technique employed. This non-invasive procedure takes between 10 and 20 minutes, is painless, and can be performed in either a doctor's office or an outpatient facility. The intense heat of the laser causes some areas of the eye's drain to shrink, resulting in adjacent areas stretching open and permitting the fluid to drain more easily. Complications are few, which is why this procedure has become increasingly popular.

The major invasive surgical technique is a glaucoma filtration procedure called trabeculectomy. In this procedure, the surgeon makes an opening by removing a small section of the trabecular meshwork, the eye's drain. By penetration of the sclera, the anterior chamber is reached and aqueous fluid can be released to a subconjunctival space. This procedure is usually done under local anaesthesia. In some patients, surgery is about 80-90% effective in lowering pressure. Although trabeculectomy is a relatively safe surgical procedure, about 30-50% of patients develop cataracts within five years of surgery. Approximately 10-15% of patients require additional surgery.

Newer surgical techniques, such as viscocanalostomy and deep sclerectomy, avoid penetration of the trabecular meshwork (D H Johnson and M Johnson, Glaucoma surgery and aqueous outflow: how does non-penetrating glaucoma surgery work?, Arch Ophthalmol (2002) 120(1):67-70). In viscocanalostomy, highly viscous hyaluronic acid compositions are used to prevent healing and postoperative scarring of the channel that is formed within the tissue. This procedure reduces complications seen with trabeculectomy. Viscocanalostomy involves creation of a large scleral flap (after conjunctival opening) of about one third of the scleral thickness; performing a second scleral excision inside the first flap up to a thin scleral layer covering the choroid; preparation of this flap into the roof of Schlemm (unroofing) and into the cornea, thus creating a "Descemet's window"; expanding Schlemm's canal with hyaluronic acid; and suturing of the first scleral flap. The many steps make the procedure difficult and time-consuming.

In a minority of patients, various types of drainage implants, made of inter alia metal, plastics, silicon or collagen, are inserted. These may help avoiding inflammation and scar formation that prevent successful drainage of the aqueous fluid.

Optionally, healing of the created channel and scar formation may be prevented by addition of chemicals, such as Mitomycin C and 5-fluorouracil (5-FU).

US patent application publication 2002/0072673 A1 and U.S. Pat. Nos. 5,360,399 and 6,375,642 B1 are concerned with viscocanalostomy.

U.S. Pat. No. 6,558,342 B1 discloses an intraocular tube, which upon implantation may be used to inject fluid or viscoelastic material into to the anterior chamber or under the conjunctiva.

U.S. Pat. No. 6,142,969 discloses implantation of a fluid shunting device into the anterior chamber. During the procedure, a channel is created, which optionally is filled temporarily with a viscoelastic substance to prevent backflow of aqueous humour before the device is inserted.

U.S. Pat. No. 5,360,425 discloses insertion of a needle to the subconjunctival space and infusion of a fluid, such as sodium hyaluronate. Thereafter, a fistula is created by ablation of the sclera employing laser pulses from an optic fibre.

U.S. Pat. No. 4,955,883 discloses that a fistula can be perpetuated in the sclera using a combination of goniopuncture and cauterisation. During this procedure, the anterior chamber can be filled with a viscoelastic material.

U.S. Pat. No. 4,716,154 discloses that a gel of cross-linked hyaluronic acid can be used as a substitute for vitreous humour. U.S. Pat. No. 5,092,837 discloses that a viscoelastic substance can be instilled in the anterior chamber to prevent collapse during insertion of a permanent implant. U.S. Pat. No. 5,811,453 discloses that injection of viscoelastic materials in the anterior chamber ameliorates inflammatory conditions resulting from glaucoma filtration surgery.

EP 1 129 683 A1 discloses injectable compositions of hyaluronic acid gel which are useful as artificial vitreous bodies. U.S. Pat. No. 5,827,937 discloses a viscoelastic gel comprising cross-linked hyaluronic acid that is useful in eye surgery. WO 98/26777 discloses a composition that is injected into the anterior chamber during eye surgery.

U.S. Pat. No. 6,383,219 discloses an implant made of cross-linked hyaluronic acid, which is useful for deep sclerectomy for draining aqueous humour during surgical treatment of glaucoma.

US patent application publication 2003/0211166 A1 discloses compositions of microspheres formed of cross-linked hyaluronic acid. The compositions are allegedly designed to be injected into Schlemm's canal.

U.S. Pat. No. 6,495,608 and WO 92/00745 discloses injection of a viscoelastic composition into the anterior or posterior chamber, which composition is removed at the end of surgery.

C Raitta et al, Acta Opthalmologica 66:544-551 (1988), discloses subconjuctival injection of cross-linked hyaluronic acid in rabbits without change of IOP.

WO2004/026347 discloses surgical creation of a channel between the anterior chamber and ocular veins in the sclera.

Known invasive treatments have some drawbacks in that they are complicated and time-consuming. Moreover, invasive treatment of glaucoma is not very effective, since the created channels tend to heal and form scars.

SUMMARY OF THE INVENTION

It is an object of the present invention to provide a novel method of treating increased intraocular pressure in the eye of a human or an animal in need thereof.

It is also an object of the present invention to provide a method of treating increased intraocular pressure in the eye of a human or an animal in need thereof, which is rapid and cost-effective.

It is one object of the present invention to provide an improved method of penetrating sclerostomy, which avoids drawbacks and/or complications with known methods.

It is also an object of the present invention to provide an improved method of penetrating sclerostomy that provides a durable lowering of increased intraocular pressure.

It is another object of the present invention to provide a method of treating increased intraocular pressure in the eye of a human or an animal in need thereof by administration of a suitable medium.

It is yet another object of the present invention to provide use of a medium for the manufacture of a medicament, such as a medical device, for treatment of increased intraocular pressure.

For these and other objects that will be evident from the following disclosure, the present invention provides according to one aspect a method of treating increased intraocular pressure in the eye of a human or an animal in need thereof, comprising the step of:
(i) injecting a viscoelastic medium into at least one sclerally penetrating fistula in said eye such that said fistula is filled with said medium.

According to another aspect, the invention provides a method of treating increased intraocular pressure in the eye of a human or an animal in need thereof, comprising the steps of:
(i) creating at least one sclerally penetrating fistula in said eye; and
(ii) injecting a viscoelastic medium into said at least one fistula such that said fistula is filled with said medium.

In a preferred embodiment of this method, said creating of at least one fistula of step (i) is immediately followed by said injecting of said medium of step (ii).

In preferred methods according to the invention, the fistula is created by penetration of the sclera following surgical displacement of the conjunctiva. In other preferred methods according to the invention, the fistula is created by penetration of both the sclera and the conjunctiva. In all methods, the resulting scleral fistula is filled with the viscoelastic medium according to the invention.

Thus, the invention resides in the finding that treatment of increased intraocular pressure can advantageously be conducted by administration of a viscoelastic medium into one or more penetrating fistulae, i.e. full-thickness fistulae. The fistulae according to the invention extend through the sclera, i.e. distal to the sclerocorneal limbus, and optionally through the conjunctiva, and a viscoelastic medium is injected into the fistulae. This rapid procedure leaves the viscoelastic medium in the sclerally penetrating fistulae, which prevents healing of the fistulae and accompanying scar formation.

According to one embodiment of the invention, said at least one fistula extends between a position distal to the sclerocorneal limbus and the anterior chamber of said eye. According to another embodiment of the invention, said at least one fistula extends between a position distal to the sclerocorneal limbus and the posterior chamber of said eye. According to yet another embodiment of the present invention, said at least one fistula extends between a position distal to the sclerocorneal limbus and the vitreous body of said eye.

In a specific embodiment of the present invention, said methods according to the invention are for treatment of glaucoma in the eye of a human or an animal.

According to yet another aspect of the present invention, there is provided a novel use of a viscoelastic medium for the manufacture of a medicament, such as a medical device, for treatment of increased intraocular pressure in the eye of a human or an animal by administration of said medicament into at least one sclerally penetrating fistula of said eye such that said fistula is filled with said medicament.

According to an embodiment of the present invention, said viscoelastic medium is selected from the group consisting of media comprising stabilized polysaccharides and derivatives thereof. In particular embodiments, said viscoelastic medium is selected from media comprising stabilized glycosaminoglycans and derivatives thereof. In other particular embodiments, said viscoelastic medium is selected from the group consisting of media comprising stabilized hyaluronic acid, stabilized chondroitin sulphate, stabilized heparin, and derivatives thereof. In a specific embodiment, said viscoelastic medium is selected from the group consisting of media comprising cross-linked hyaluronic acid and derivatives thereof.

In preferred embodiments of the invention, said viscoelastic medium is present as gel particles.

Preferably, said medicament is for treatment of glaucoma in the eye of a human or an animal.

DETAILED DESCRIPTION OF THE INVENTION

Figure 1:
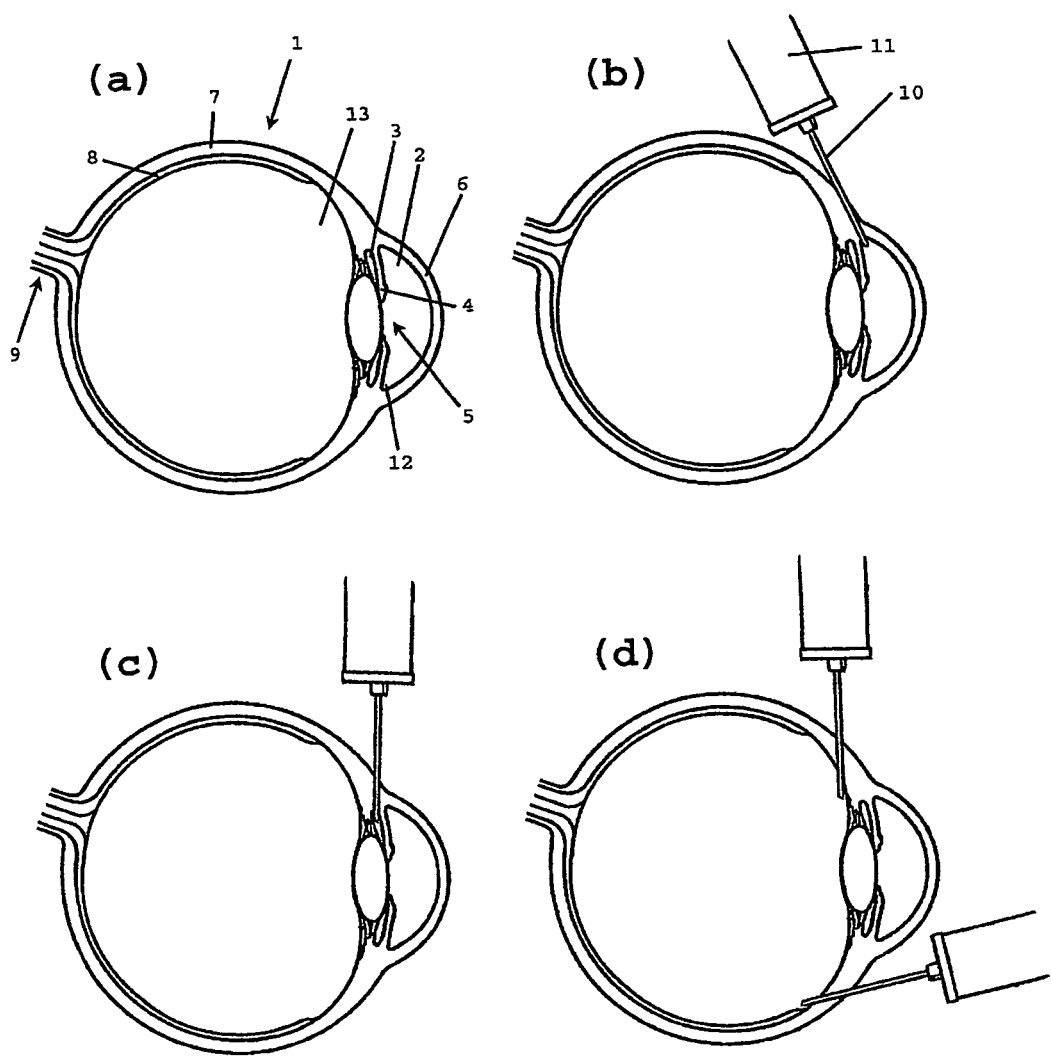
FIG. 1 depicts cross-sectional views of an eye bulb and creation of fistulae according to the invention.

The present invention concerns an improved method for treatment of increased intraocular pressure, which is typically associated with glaucoma. In essence, the method involves administration of a viscoelastic medium into a sclerally penetrating fistula. According to another aspect, the invention resides in an innovative combination of penetrating sclerostomy and administration of a viscoelastic medium into the resulting fistula.

In its most general form, the invention provides a method of treating increased intraocular pressure in the eye of a human or an animal in need thereof, comprising the step of:
(i) injecting a viscoelastic medium into at least one sclerally penetrating fistula in said eye such that said fistula is filled with said medium.

According to another aspect, the invention provides a method of treating increased intraocular pressure in the eye of a human or an animal in need thereof, comprising the steps of:
(i) creating at least one sclerally penetrating fistula in said eye; and
(ii) injecting a viscoelastic medium into the at least one fistula such that said fistula is filled with said medium.

In preferred methods according to the invention, the fistula is created by penetration of both the conjunctiva and the sclera. In other preferred methods according to the invention, the fistula is created by penetration of the sclera. In the latter methods, the conjunctiva has been made not to cover the sclera at the penetration site. For practical purposes, this means that the conjunctiva has been temporarily displaced by a suitable surgical procedure. Following the formation of a scleral fistula filled with the viscoelastic medium according to the invention, the conjunctiva is surgically restored or is allowed to heal spontaneously.

As used herein, the term "treating" involves any kind of preventive, alleviating or curative treatment.

As used herein, the term "intraocular pressure", or "IOP", refers to the pressure inside the eye. The intraocular pressure is routinely measured by ophthalmologists using the assumption that the pressure required to flatten a given area of the cornea. Normal eye pressures range from about 10 to 21 mm Hg. Accordingly, the term "increased intraocular pressure" refers to intraocular pressures exceeding the normal range of 10-21 mm Hg.

In an embodiment of the invention, the method is for treating glaucoma or elevated intraocular pressure associated with glaucoma. The invention is useful for treatment of all types of glaucoma where invasive treatment is an option, including open-angle glaucoma, angle-closure glaucoma, secondary glaucoma, etc.

By the term "creating" is meant any type of invasive activity resulting in the creation of a fistula, including use of traditional instruments. Instruments that are useful according to the present invention include needles, cannulas, knives, scalpels, etc. The fistula is created from the exterior of the eye, i.e. from the outside of the conjunctiva or sclera, to the interior of the eye, i.e. to the anterior or posterior chambers or the vitreous body.

By term "sclerally penetrating fistula", as used herein, is meant a non-natural, created passage, i.e. a channel or tract, formed directly in the scleral tissue. Thus, the fistula does not involve any artificial tube or the like. By using a tissue channel rather than an artificial tube, irritation and clogging of the channel can be decreased or avoided. The fistula extends throughout the sclera to the interior of the eye. Thus, the exterior opening of the sclerally penetrating fistula according to the invention is arranged subconjunctivally, distal to the sclerocorneal limbus and proximal to the choroid and the retina, typically 4-7 mm from the limbus. The interior opening of the fistula is arranged in the anterior or posterior chamber of the eye. Alternatively, the interior opening is arranged in the vitreous body of the eye.

Alternatively, the conjunctiva may be surgically displaced, a sclerally penetrating fistula is created and filled with a medium according to the invention, and the conjunctiva is restored to its original place. This creates a subconjunctival drainage from the interior of the eye, e.g. the anterior chamber, maintains the medium according to the invention in the fistula, and maintains a suitable IOP.

The terms "proximal" and "anterior" have their standard meaning in the field of ophthalmology, i.e. referring to objects closer to the front of eye (i.e. the cornea). In contrast, the terms "distal" and "posterior" refer to objects closer to the back of eye (i.e. the area surrounding the optic nerve).

According to the invention, the ophthalmologist may create one or more sclerally penetrating fistula (e). It more than one fistula is created, the fistulae may be created during the same procedure or at different occasions. Moreover, the fistulae may end in the same chamber or may end in different chambers. Optionally, the fistula (e) may end in the vitreous body. The number and arrangement of the fistulae are decided by the ophthalmologist depending on several considerations, including the width of the fistula and the desired intraocular pressure lowering effect.

In certain methods according to the invention, the created fistula does not penetrate any visible ocular veins in the sclera. In order to decrease irritation and/or pain, it is advantageous to avoid, as far as possible, direct contact with blood during the procedure. Penetration of the ciliary body shall also be avoided.

In certain embodiments of the method, penetration of the trabecular meshwork is avoided. In certain other embodiments, the trabecular meshwork may be penetrated. It shall be noted that this penetration involves the making of a full-thickness, scleral fistula of limited width, typically the size of a cannula, e.g. 32-18 gauge. Without administration of the viscoelastic medium according to the invention, the fistula would quickly heal, whereas administration of the viscoelastic medium into the fistula prevents healing and makes the fistula permanent.

In contrast, trabeculectomy involves cutting out a segment of the sclera and removing it permanently, and an artificial lake is created between the sclera and the conjunctiva. The scleral space that is created in trabeculectomy is too large to heal spontaneously.

In a first embodiment, a fistula according to the invention is created with a suitable instrument, such as a needle, through the conjunctiva and the sclera into the anterior chamber. In a second embodiment, a fistula according to the invention is created with a suitable instrument, such as a needle, through the conjunctiva and the sclera into the posterior chamber. In a third embodiment, a first fistula according to the invention is created with a suitable instrument, such as a needle, through the conjunctiva and the sclera into the anterior chamber, and a second fistula according to the invention is created with a suitable instrument, such as a needle through the conjunctiva and the sclera into the posterior chamber.

In alternative embodiments, the conjunctiva is surgically displaced (temporarily), and a fistula according to the invention is created with a suitable instrument through the sclera. Following administration of a medium according to the invention into the fistula, the conjunctiva is restored to its original place.

By the term "viscoelastic medium", as used herein, is meant a medium that exhibits a combination of viscous and elastic properties. As is well known by the skilled man, the viscoelastic properties can be determined with a rheometer. In oscillating mode, the elastic modulus (G') and the viscous modulus (G") can be determined at a frequency of 1 Hz. For a viscoelastic medium according to the invention, the following relationship is satisfied:

$$0.05 \leq \frac{G'}{(G'' + G')} \leq 0.95,$$

preferably $$0.1 \leq \frac{G'}{(G'' + G')} \leq 0.9.$$

Specifically, the viscoelastic medium according to the invention is injectable through a 32-18 gauge needle by application of a pressure of 1-50 N. In particular, the medium, or a medicament, such as a medical device, comprising the medium, is injectable into a sclerally penetrating fistula according to the invention such that said fistula is filled with said medium or medicament.

Viscoelastic media according to the invention include gels, solutions, suspensions, slurries and mixtures. The medium includes a physiological salt solution and optionally other active substances, such as cytotoxic substances, anti-inflammatory substances, etc. Suitable viscoelastic media also include media containing stabilized dextran and derivatives thereof, such as dextranomer. The media containing dextranomer may be in the form of particles.

Viscoelastic media according to the invention include, without being limited thereto, media containing stabilized polysaccharides and derivatives thereof. In such media, the polysaccharide, or at least one of the polysaccharides, provides the viscoelastic properties of the medium. Suitable viscoelastic media contain stabilized derivatives of starch. Suitable viscoelastic media can also contain stabilized glycosaminoglycans and derivatives thereof, such as stabilized hyaluronic acid, chondroitin sulphate and heparin, and derivatives thereof. The viscoelastic medium may also be a combination of two or more suitable viscoelastic media.

By the term "stabilized", as used herein, is meant any form of chemical stabilization that, under physiological conditions, renders the polysaccharide more stable to degradation than the parent compound. Stabilized polysaccharides and derivatives thereof include e.g. cross-linked and partially cross-linked polysaccharides and derivatives thereof.

By the term "derivative", as used herein, is meant any suitable form of derivative of a polysaccharide, including cross-linked and substituted polysaccharides, such as a sulphated polysaccharide.

Viscoelastic media according to the invention are biocompatible, sterile and readily injectable through standard needles used in medicine, such as 32-18 gauge needles. Optionally, the polysaccharide of the viscoelastic medium is of non-animal origin. Advantageously, the polysaccharides of the viscoelastic media according to the invention are stable, but not permanent, under physiological conditions. According to an embodiment of the invention, at least 50%, preferably at least 70%, more preferably at least 90%, of the polysaccharides providing viscoelasticity to the medium remains for at least two weeks in vivo, more preferably between two weeks and two years. The polysaccharide(s) providing viscoelasticity to the medium according to the invention is preferably degraded after five years or more in vivo. The term "degraded" implies that less than 20%, preferably less than 10%, of the polysaccharide remains in the body. Thus, the viscoelastic medium will not remain permanently in the tissue. It will eventually be degraded following the formation of a permanent scleral fistula.

The polysaccharide of the viscoelastic medium according to the invention is preferably more resistant to degradation in vivo than natural hyaluronic acid. The prolonged presence of the stable polysaccharide providing viscoelasticity prevents healing of the created channels and thereby improves the outcome of the treatment.

A preferable viscoelastic medium according to the invention contains cross-linked hyaluronic acid and derivatives thereof. One type of suitable cross-linked hyaluronic acid is obtainable by cross-linking of hyaluronic acid, optionally non-animal, using the method of U.S. Pat. No. 5,827,937.

In brief, said method involves forming an aqueous solution or suspension of a water soluble, cross-linkable polysaccharide; initiating a cross-linking of the polysaccharide in the presence of a polyfunctional cross-linking agent; sterically hindering the cross-linking reaction from terminating before gelation occurs, whereby an activated polysaccharide is obtained; and reintroducing sterically unhindered conditions for the activated polysaccharide so as to continue the cross-linking thereof up to a viscoelastic gel.

The cross-linking agent to be used in connection with this particular method is any previously known cross-linking agent useful in connection with polysaccharides, consideration being taken to ensure that the biocompatibility prerequisites are fulfilled. Preferably, however, the cross-linking agent is selected from the group consisting of aldehydes, epoxides, polyaziridyl compounds, glycidyl ethers and divinylsulfones. Of these, glycidyl ethers represent an especially preferred group, of which 1,4-butanediol diglycidyl ether can be referred to as a preferred example.

In this particular method, the initial cross-linking reaction in the presence of a polyfunctional cross-linking agent can be performed at varying pH values, primarily depending on whether ether or ester reactions should be promoted.

In a preferred embodiment of the invention, the viscoelastic medium is present as gel particles or gel-like particles of any shape. A major volume, or more than 50% (v/v), of the particles have a size of at least 10 μm, preferably in the range of 10 μm-5 mm, such as in the range of 10 μm-0.9 mm, more preferably in the range of 0.15-0.95 mm in the presence of a physiological salt solution. In preferred embodiments, more than 70% (v/v), preferably more than 90% (v/v), of the particles are within the given size limits under physiological conditions.

It follows that in certain embodiments of the invention, the created fistula is filled with a large number of small gel particles. In certain other embodiments, the fistula is filled with only a few gel particles. It is even a possibility that the entire fistula is filled with one large particle of any suitable shape.

It goes without saying that the size of the gel particles according to the invention is dependent upon e.g. the ionic strength and pH of the solvent, solution or carrier that is included in and/or surrounding the gel particles. Throughout this specification, given particle sizes assume physiological conditions, particularly isotonic conditions. It shall be noted that, while it is preferred that the gel particles contain and are dispersed in a physiological salt solution, it is contemplated that the gel particles according to the invention can temporarily be brought to different sizes by subjecting the gel particles to a solution of another tonicity. Particles that are within the scope of this invention exhibit a particle size within the given ranges under physiological conditions, e.g. when administrated sclerally in the body or when subjected to a physiological, or isotonic, salt solution, i.e. a solution with the same tonicity as the relevant biological fluids, e.g. isoosmotic with serum.

In certain embodiments of the invention, essentially all fluid may be incorporated in gel particles, which means that the viscoelastic medium will consist of the gel particles essentially without any free fluid.

As used herein, a physiological, or isotonic, solution is a solution having an osmolarity in the range of 200-400 mOsm/l, preferably 250-350 mOsm/l, more preferably approximately 300 mOsm/l. For practical purposes, this osmolarity is easily achieved by preparation of a 0.9% (0.154 M) NaCl solution.

When the viscoelastic medium is present as particles of a cross-linked hyaluronic acid, a major volume, or more than 50% (v/v), preferably more than 70% (v/v), more preferably more than 90% (v/v) of the particles have a size smaller than 5 mm, preferably smaller than 0.9 mm, preferably in the range of 10 μm-0.9 mm, more preferably in the range of 0.15-0.95 mm.

A suitable way of obtaining a desired particle size involves producing a gel made of cross-linked hyaluronic acid at a desired concentration and subjecting the gel to physical disruption, such as mincing, mashing or allowing the gel to pass through a filter with suitable particle size. The resulting gel particles are dispersed in a physiological salt solution, resulting in a gel dispersion or slurry with particles of desired size.

Particle size may be determined in any suitable way, such as by laser diffraction, microscopy, filtration, etc, and is decided by the longest distance between two ends of the particle. The specific shape of the gel particles is not critical. For spherical particles, the diameter equals the size for this purpose. The size range may be regulated by mechanical disruption, such as mincing, mashing, filtration, etc, of a gel of a suitable concentration of the desired viscoelastic medium.

Another aspect of the invention is the hardness of the gel. The gel hardness can readily be regulated by adjustment e.g. of the concentration and type of cross-linking agent, if any. Thus, harder gels can be achieved by a higher degree of cross-linking in the gel. Other factors influencing the hardness of the gel are e.g. pH and temperature. Harder gels and particles made thereof are generally less viscoelastic and have a longer half-life in vivo than softer gels. For use in the present invention, it is critical that the gel retains enough viscoelastic properties so that it is still injectable.

When the injectable medium is a hyaluronic acid medium, the hyaluronic acid concentration is 5 mg/ml or higher. It is preferred that the hyaluronic acid concentration is in the range of 5-100 mg/ml, more preferred 10-50 mg/ml, such as approximately 20 mg/ml.

According to the invention, the viscoelastic medium is injected in the previously created fistula (e). The viscoelastic medium may be injected immediately following the creation of the fistula or at a later occasion. Optionally, viscoelastic medium in the fistula may be replaced, refilled or replenished by a subsequent injection of the same or another viscoelastic medium.

The fistula is filled with the medium according to the invention. By the term "filled" is meant that the medium is administrated throughout at least the scleral part of the fistula. Optionally, both the scleral and the conjunctival part, if any, of the fistula are filled with the medium.

The injected volume is determined by the number and size of the fistulae. In a typical fistula, created with a 27 gauge needle, a volume in the range of 1-10 μl is typically injected. For other needle sizes, the volume is adapted to the size of the fistula, such as in the range of 0.1-50 μl, typically 0.1-10 μl. Without being limited thereto, a fistula according to the invention typically have a diameter in the range of 0.1-2.0 mm, such as 0.2-1.0 mm, and a length in the range of 2-15 mm, such as 3-10 mm.

The injected viscoelastic medium is not withdrawn from the fistula by the ophthalmologist; rather, the medium is left in the fistula, where it prevents healing and/or scar formation and allows for durable intraocular pressure lowering. Thus, a preferred method according to the invention involves the additional step of leaving said medium in the created fistula.

With reference to the drawings, FIG. 1a shows a sectional view of an eye (1), where the anterior and posterior chambers (2,3) of the eye (1) are separated by the iris (4) and the pupil (5). Evident in the figure are also the cornea (6), the sclera (7), the retina (8) and the optic nerve (9). FIG. 1b-d shows various possibilities for the sclerally penetrating fistula, which is created in certain methods of treatment according the invention. The fistula is created with a needle (10), which is connected to a syringe (11) containing the viscoelastic medium according to the invention.

In an advantageous embodiment of the invention, the fistula is created using a standard needle (10), and the viscoelastic medium is continuously injected into the fistula from a syringe (11) coupled to the needle (10) while the needle (10) is withdrawn, resulting in a penetrating fistula filled with the viscoelastic medium.

The method involves insertion of a needle (10) into the sclera (7) of the eye (1), 4-7 mm behind the limbus (the junction between the sclera (7) and cornea (6)). As shown in FIG. 1b, the needle (10) is made to penetrate the sclera (7) and reach the anterior chamber angle (12). During withdrawal of the needle (10), the viscoelastic medium is continuously expelled sclerally throughout the length of the fistula. Thereby, improved drainage of aqueous humour is achieved easily and rapidly. Also, the created drainage is prevented from healing by the expelled viscoelastic substance. Thereby, a long-lasting or permanent fistula is created, which allows for sufficient drainage of aqueous humour.

In an alternative embodiment, shown schematically in FIG. 1c, the needle (10) is made to penetrate the sclera (7) and reach the posterior chamber (3). During withdrawal of the needle (10), the viscoelastic medium is continuously expelled sclerally in the thus created fistula.

In another embodiment, shown schematically in FIG. 1d, the needle (10) is made to penetrate the sclera (7) and reach the vitreous body (13). During withdrawal of the needle (10), the viscoelastic medium is continuously expelled sclerally in the resulting fistula. In FIG. 1d, two alternative ways of creating the fistula are shown.

It shall be noted that while traditional surgical treatments involves creation and closure of a scleral flap, surgical removal of tissue and creation of channels, the present method involves direct penetration of the sclera using e.g. a needle or a cannula. This procedure simplifies the creation of a drainage channel.

Without being limited thereto, the present invention will in the following be further illustrated by way of examples.

EXAMPLES

Example 1

Preparation of Non-Animal Stabilized Hyaluronic Acid

As previously exemplified in e.g. U.S. Pat. No. 5,827,937, 10 g of hyaluronic acid prepared by fermentation of Streptococcus was dispersed in 100 ml of 1% NaOH, pH>9. Cross-linking agent in the form of 1,4-butanediol diglycidyl ether was added to a concentration of 0.2%. The resulting composition was incubated at 40° C. for 4 h.

The incubated composition was diluted with an acidic water solution to reach neutral pH under mixing, yielding a final hyaluronic acid concentration of 20 mg/ml, and again incubated for 12 h at 70° C. The viscoelastic slurry that resulted from this second incubation was then cooled to room temperature and mashed to its final particle size, approximately 0.8 mm.

Example 2

Pre-Clinical Study of Non-Animal Stabilized Hyaluronic Acid in a Rabbit Eye

The objective of the study is to show that injections of a viscoelastic composition, such as non-animal stabilized hyaluronic acid, in the eye will provide a functional drainage model for glaucoma treatment.

Figure 2:
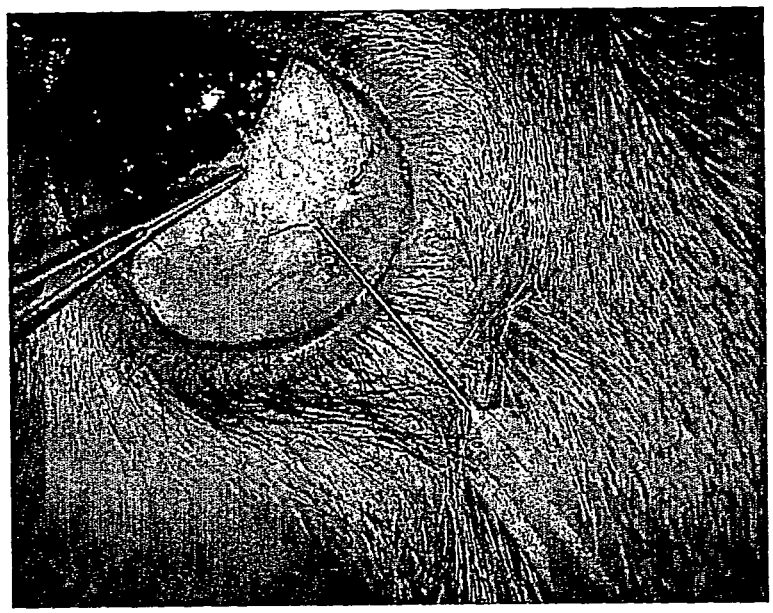
FIG. 2 is a photograph displaying creation of a fistula according to the invention.

18 rabbits divided in three groups were used in the study. The rabbits were anesthetized according to standard procedures. The composition, 20 mg/ml of the non-animal stabilized hyaluronic acid obtainable by the method of example 1 (commercially available from Q-Med AB, Uppsala, Sweden), was injected in one eye and the opposite eye was the untreated control. As shown in FIG. 1b and FIG. 2, an approximately 5 mm long fistula was created with a needle in the sclera by penetrating the conjunctiva and moving the needle through the sclera to the angle of the anterior chamber. The composition was injected into the sclera of the eye during withdrawal of the needle, thereby filling the fistula with the composition. The needles used were 27, 23 and 18 gauge needles.

The goal was to create a drainage from the anterior chamber to the subconjunctival tissue. The amount of composition used, size and type of needle and injection site was recorded. The injection site was checked visually before and after injection. The animals were observed daily according to standard procedures.

Figure 3A:
FIG. 3A is a photograph of a histological tissue section encompassing a fistula according to the invention, stained with biotin-labelled hyaluronic acid binding protein (HABP) using avidin-biotin-peroxidase and DAB.
Figure 3B:
FIG. 3B is a photograph of a histological tissue section encompassing a fistula according to the invention, stained with haematoxylin and eosin.

At weeks 8 and 16, nine of the animals were examined and euthanized, and histological samples were taken from the injection sites. Photographs of the histological samples are shown in FIG. 3. The fistulae, shown in cross-sections in FIG. 3, were maintained after 8 as well as 16 weeks and still contained the stabilized hyaluronic acid, as seen in FIG. 3A (staining using hyaluronic acid binding protein). Cells had not penetrated into the fistulae. There was no evidence of adverse tissue reactions, nor formation of tissue within the fistulae.

In the samples collected after 16 weeks of exposure to the composition, histochemical staining (FIG. 3B, staining with haematoxylin and eosin) indicated that the walls of the fistulae were covered with endothelial cells, i.e. an early sign that the fistulae may be permanent.

Example 3

Pre-Clinical Study of Stabilized Hyaluronic Acid in a Rabbit Eye

Rabbits are anesthetized according to standard procedures. The compositions used are slurries containing stabilized hyaluronic acid gel particles with a hyaluronic acid concentration of 10, 30, and 50 mg/ml, respectively. The compositions are injected in one eye and the opposite eye is the untreated control. In each slurry, a major volume of the particles are approximately 0.1, 0.4 and 0.8 mm, respectively.

1-3 fistulae per eye is (are) created with a needle in the sclera by penetrating the conjunctiva and moving the needle through the sclera to the anterior (FIG. 1b) or posterior chamber (FIG. 1c). The composition is injected into the sclera of the eye during withdrawal of the needle.

The amount of composition used, size and type of needle and injection site is recorded. The injection site is checked visually before and after injection.

The animals are observed daily according to standard procedures. At week 8 and 16, animals are examined and euthanized, and histological samples are taken from the injection sites.

Example 4

Administration of Stabilized Hyaluronic Acid in a Rabbit Eye

The general procedure of example 2 was followed using three different cannula sizes: 18G, 23G and 27G was used. The diameter of the channel formed was approximately equal for all cannulas. The size of the channel seems to be more dependent on the amount of material injected than the diameter of the cannula. Persistent channels were found in 2/3 eyes with 18G, 2/3 eyes with 27G and 3/3 eyes with 23G cannula.

Example 5

Fluid Flow Through Gel Particles of Stabilized Hyaluronic Acid

The extrusion force for an aqueous composition containing 20 mg/ml of a non-animal stabilized hyaluronic acid obtainable by the method of example 1 (commercially available from Q-Med AB, Uppsala, Sweden), in the form of gel particles (average diameter 400 µm) was determined to 21 N through a 30 gauge needle, and 4 N through a 23 gauge needle.

In the first set of experiments, the possibility of flow through the gel particles was studied by applying a flow of saline through the gel particles by means of a pump. A glass column (diameter 5 mm) was filled with gel particles to a height of 30 mm (approximately 1 ml gel particles). The flow of saline through the gel particles was controlled with a pump. Saline was able to flow through this column with a flow rate of 125 µl/min.

In the second set of experiments, a glass column (diameter 10 mm) was filled with 1 ml of the composition, and an aqueous solution of 0.9% NaCl was applied at a pressure of 29 mm Hg, a pressure corresponding to the IOP with untreated glaucoma. This pressure resulted in a flow of 160 µl/h (2.7 µl/min) through the composition. For comparison, the aqueous humour flow in a healthy eye is in the range of 1.8-4.3 µl/min, typically 2.75 µl/min (Brubaker R F, "Flow of aqueous humor in humans [The Friedenwald Lecture]", Investigative Ophthalmology & Visual Science 32:3145-3166 (1991)).

The experiments performed demonstrate that saline can flow through gel particles after application of a pressure of 29 mm Hg. The flow rate is of the same magnitude as the aqueous humour flow in normal human eyes. Without being bound to any particular theory, it is contemplated that the saline will flow between the gel particles in the same way as solvent flows through chromatographic gel beads, such as Sephadex, in size exclusion chromatography.

The invention claimed is:
1. A method of treating increased intraocular pressure in the eye of a human or animal in need thereof, comprising the step of:
 (i) injecting a viscoelastic medium directly into at least one sclerally penetrating fistula which extends throughout the sclera to the interior of the eye such that said fistula following said injection is filled with said medium, wherein said fistula achieves drainage of aqueous humor from the eye to lower increased intraocular pressure, and said injecting is performed by releasing the viscoelastic medium from a needle as the needle is withdrawn from the fistula.
2. A method according to claim 1, wherein said at least one fistula extends between a position distal to the sclerocorneal limbus and the anterior chamber of said eye.
3. A method according to claim 2, wherein said viscoelastic medium is selected from the group consisting of media comprising stabilised polysaccharides and derivatives thereof.
4. A method according to claim 2, wherein said injecting of said medium of step (i) immediately follows a step of creating the at least one sclerally penetrating fistula.

5. A method according to claim 1, wherein said at least one fistula extends between a position distal to the sclerocorneal limbus and the posterior chamber of said eye.

6. A method according to claim 1, wherein said at least one fistula extends between a position distal to the sclerocorneal limbus and the vitreous body of said eye.

7. A method according to claim 1, wherein said viscoelastic medium is selected from the group consisting of media comprising stabilised polysaccharides and derivatives thereof.

8. A method according to claim 7, wherein said viscoelastic medium is selected from media comprising stabilised glycosaminoglycans and derivatives thereof.

9. A method according to claim 8, wherein said viscoelastic medium is selected from the group consisting of media comprising stabilised hyaluronic acid, stabilised chondroitin sulphate, stabilised heparin, and derivatives thereof.

10. A method according to claim 9, wherein said viscoelastic medium is selected from the group consisting of media comprising cross-linked hyaluronic acid and derivatives thereof.

11. A method according to claim 1, wherein said viscoelastic medium is present as gel particles.

12. A method according to claim 1 for treatment of glaucoma in the eye of a human or an animal.

13. A method of treating increased intraocular pressure in the eye of a human or animal in need thereof, comprising the steps of:
(i) creating at least one sclerally penetrating fistula in said eye wherein said fistula extends throughout the sclera to the interior of the eye; and
(ii) injecting a viscoelastic medium directly into said at least one fistula such that said fistula is filled following said injection with said medium, wherein said fistula achieves drainage of aqueous humor from the eye to lower increased intraocular pressure, and said injecting is performed by releasing the viscoelastic medium from a needle as the needle is withdrawn from the fistula.

14. A method according to claim 13, wherein said creating of at least one fistula of step (i) is immediately followed by said injecting of said medium of step (ii).

15. A method according to claim 13, wherein said at least one fistula extends between a position distal to the sclerocorneal limbus and the anterior chamber of said eye.

16. A method according to claim 13, wherein said at least one fistula extends between a position distal to the sclerocorneal limbus and the posterior chamber of said eye.

17. A method according to claim 13, wherein said at least one fistula extends between a position distal to the sclerocorneal limbus and the vitreous body of said eye.

18. A method according to claim 13, wherein said viscoelastic medium is selected from the group consisting of media comprising stabilised polysaccharides and derivatives thereof.

19. A method according to claim 18, wherein said viscoelastic medium is selected from media comprising stabilised glycosaminoglycans and derivatives thereof.

20. A method according to claim 19, wherein said viscoelastic medium is selected from the group consisting of media comprising stabilised hyaluronic acid, stabilised chondroitin sulphate, stabilised heparin, and derivatives thereof.

21. A method according to claim 20, wherein said viscoelastic medium is selected from the group consisting of media comprising cross-linked hyaluronic acid and derivatives thereof.

22. A method according to claim 13, wherein said viscoelastic medium is present as gel particles.

23. A method according to claim 13 for treatment of glaucoma in the eye of a human or an animal.

* * * * *